United States Patent [19]

Nonboe

[11] Patent Number: 5,344,780
[45] Date of Patent: Sep. 6, 1994

[54] METHOD FOR DETERMINING INDOLE COMPOUNDS ASSOCIATED WITH BOAR TAINT IN PORK AS WELL AS A SAMPLE CONTAINER TO BE USED IN THE METHOD

[76] Inventor: Ulf Nonboe, Nyvej 9, DK-1851 Frederiksberg C, Denmark

[21] Appl. No.: 974,590
[22] PCT Filed: Aug. 20, 1991
[86] PCT No.: PCT/DK91/00237
§ 371 Date: Feb. 19, 1993
§ 102(e) Date: Feb. 19, 1993
[87] PCT Pub. No.: WO92/03729
PCT Pub. Date: Mar. 5, 1992

[30] Foreign Application Priority Data

Aug. 22, 1990 [DK] Denmark ............... 2008/90

[51] Int. Cl.$^5$ ................. G01N 33/04; G01N 33/08
[52] U.S. Cl. ......................... 436/21; 436/20; 436/175; 436/178; 436/96; 422/101; 422/102
[58] Field of Search ............. 436/20, 21, 161, 172, 436/175, 178, 96, 97; 422/99, 101, 102; 215/DIG. 8; 206/222

[56] References Cited

U.S. PATENT DOCUMENTS

| | | | |
|---|---|---|---|
| 3,220,588 | 11/1965 | Lipari | 215/DIG. 8 X |
| 3,347,410 | 10/1967 | Schwartzman | 206/222 X |
| 3,521,745 | 7/1970 | Schwartzman | 215/DIG. 8 X |
| 3,713,780 | 1/1973 | Shapiro | 422/102 X |
| 3,715,189 | 2/1973 | Nighohossian et al. | 422/102 X |
| 4,102,451 | 7/1978 | Clarke et al. | 215/DIG. 8 X |
| 4,177,938 | 12/1979 | Brina | 206/222 X |
| 4,234,083 | 11/1980 | Cohen | 215/DIG. 8 X |
| 4,258,845 | 3/1981 | Potts | 215/DIG. 8 X |
| 4,266,423 | 5/1981 | Hadden | 436/21 X |
| 4,294,351 | 10/1981 | Cheethan | 206/222 |
| 4,321,139 | 3/1982 | Auclair | 422/101 X |
| 4,384,206 | 5/1983 | Bjarno | 250/339 |
| 4,563,428 | 1/1986 | Mortensen | 436/21 |
| 4,610,374 | 9/1986 | Buehler | 206/222 X |
| 4,610,877 | 9/1986 | Pearson et al. | 424/88 |
| 4,786,471 | 11/1988 | Jones et al. | 422/102 X |
| 4,906,563 | 3/1990 | Singh et al. | 435/7 |

FOREIGN PATENT DOCUMENTS

| | | |
|---|---|---|
| 154667 | 3/1983 | Denmark . |
| WO80/02597 | 11/1980 | PCT Int'l Appl. . |
| WO83/00928 | 3/1983 | PCT Int'l Appl. . |

OTHER PUBLICATIONS

Dialog Information Service, File 305: Analytical Abstracts; accession No. 134350, AA accession No. 49-0-8-F-00042, Schulz, H., "Determination of indole and skatole (3-methylindole) in seafood by HPLC"; from Z. Lebensm.-Unters.-Forsch., 183(5):331-34. published Nov. 1986.

Derwent abstract, No. 87-204 312/29 SU 1 272 248, publ. week 8729 (UKR Steppe Cattle). published Nov. 23, 1986.

Primary Examiner—Lyle A. Alexander
Assistant Examiner—Maureen M. Wallenhorst
Attorney, Agent, or Firm—Willian Brinks Hofer Gilson & Lione

[57] ABSTRACT

A sample of lard or fat is taken from a carcass of a pig or part thereof and heated until the fat is liquid, whereupon the sample is extracted by a polar solvent, and the contents of the indole compounds associated with boar taint in the extract are determined. A sample container useable when carrying out the method includes a container divided into an open first chamber and a closed second chamber, where the two chambers are separated from each other by a partition wall breakable by a slight physical load. A closing device associated with the open container includes a third chamber provided at the top with an area penetrable by an injection needle and at the bottom includes a filter which may be lowered into the container. The method is simple and economically advantageous, especially for use in relatively small slaughterhouses.

13 Claims, 1 Drawing Sheet

METHOD FOR DETERMINING INDOLE COMPOUNDS ASSOCIATED WITH BOAR TAINT IN PORK AS WELL AS A SAMPLE CONTAINER TO BE USED IN THE METHOD

TECHNICAL FIELD

The present invention relates to a method for determining boar taint producing indole compounds, especially skatole and indole, in pork/lard, by which method a sample of a predetermined amount of lard or fat is taken from a carcass of a pig or part thereof and by which method the sample is extracted by means of a polar solvent, whereupon the contents of one or more indole compounds in the extract are determined, as well as a sample container to be used when carrying out the method.

TECHNICAL BACKGROUND

Cut out pieces from uncastrated boars may develop a bad smell, the so-called boar taint, when heated. In castrated boars, on the other hand, such obnoxious smells rarely appear. Male pigs are therefore usually castrated at a young age in order to prevent the meat therefrom from displaying the unpleasant boar taint when prepared later in the household. In other connections, the castration of male pigs has an unfavourable effect on the animals, as their utilization of the feeding stuff declines, their sickness rate increases and the meat percentage of the carcasses simultaneously falls.

The presence of certain indole compounds in the pork produces this very unpleasant boar taint when heated. Especially the compounds skatole and indole play a very important role. A good correlation has thus been found between the contents in the pork of skatole and indole, respectively, and the development of the boar taint. So far it has not been possible to determine these compounds specifically by a method which can be used in slaughter-houses in an economically acceptable manner.

WO 83/00928 (Slagteriernes Forskningsinstitut) discloses a method for the detection of boar taint by preparing an extract of a meat and/or fat sample, reacting said extract with a color reagent, for which the color intensity developed at certain wavelengths exhibit a statistical relationship with boar taint, determining the transmittance or absorbance of the reacted extract at one or more such wavelengths, and inserting the recorded values in the said statistical relationship.

DK patent No. 154,667 (Slagteriernes Forskningsinstitut) discloses a method for the determination of the degree of boar taint, whereby a sample of meat is extracted with a polar organic solvent, whereupon, optionally following a purification, the extract is analyzed by spectrophotometry or flourometry to determine one or more parameters which are statistically correlated with the development of boar taint. In one embodiment, (also disclosed in WO 83/00928) the degree of boar taint in pork is determined by homogenizing a weighed sample of lard and extracting said sample with tris-(hydroxymethyl)-amino-methane and acetone. A color reagent is added to the extract and the absorbance is measured spectrophotometricly in a wavelength range from 400 to 800 nm. The method is suitable for use in large slaughter-houses, where 1200–1400 samples are analyzed daily. In small slaughterhouses, where for instance less than about 500 samples are to be analyzed daily, the individual analysis will be too costly, as the analytical apparatus is expensive. By the method skatole and indole are not specifically determined, but rather the total contents of skatole equivalents of the sample.

The method disclosed in DK patent No. 154,667 is to a large extent used in Danish slaughterhouses and by means of a standardized spectrophotometric method a limit for the rejection of pigs has been set at the maximum amount of 0.25 ppm skatole equivalents.

The inventor of the present invention has carried out a regression analysis of the test results which are stated in DK patent No. 154,667 in Table I page 15 and Table II, page 17. The correlation factors thereby found are stated below.

When measuring meat extracts fluorometrically, a correlation factor to an organoleptic evaluation of the smell of 0.72 was obtained, while for lard extracts a correlation factor to an organoleptic evaluation of the smell of 0.24 was obtained. When comparing samples of lard analyzed by flourometry and by spectrophotometry, respectively, a correlation factor between the two analytical methods of 0.13 was obtained, and the correlation factor between the spectrophotometric measurement and the subjective estimate of the smell was 0.70. Calculations have been made on the basis of the results in Table II of the above DK patent of the fluorometric and spectrophotometric measurements both with and without the 8 young sows stated in page 17, lines 28–30 of the patent. Whether the calculations have been carried out with or without the 8 young sows, does, however, not change the importance of the results. A correlation factor of 1.00 corresponds to a correlation of 100%.

It may thus be concluded that the method disclosed in DK patent No. 154,667 is unsuitable for determining the degree of boar taint by spectrofluorometry on samples of lard.

It is thus the object of the present invention to provide a method for determining the degree of boar taint in pork whereby the compounds which, when heated, cause the unpleasant smell may be determined more specifically. It is thereby possible with greater certainty to point out those carcasses which, when prepared, will produce the boar taint which is unacceptable to the consumer, and thereby to prevent an unnecessary rejection of pork.

It is also the object of the present invention to provide a simple and relatively inexpensive method for the determination of the degree of boar taint, said method being especially suitable for use in small slaughter-houses which cannot bear the cost of investing in complicated and expensive analytical equipment.

Further, it is an object of the invention to provide a practical sample container for selecting a sample of fat where a prepared sample may be taken directly from the sample container, said sample being ready for injection into an analytical apparatus, for instance a HPLC apparatus.

DISCLOSURE OF THE INVENTION

The above objects are obtained by the method according to the invention for the determination in pork/lard of indole compounds, especially skatole and indole, producing boar taint, by which method a sample of a predetermined amount of lard or fat is taken from a carcass of a pig or part thereof, and by which method the sample is extracted with a polar solvent, whereupon the contents of one or more indole compounds are determined in the extract, which method is characterised in that prior to and/or during the extraction, the sample is heated until the fat is liquid.

In one embodiment of the invention a defined amount of lard is taken from the carcass, and after heating the lard until the fat has melted, the entire sample of lard is extracted with a polar solvent.

In another embodiment of the invention, a sample of lard is taken and prior to carrying out the extraction, the fat free solids of the lard are separated whereby extraction is only carried out on the liquid fatty phase thereof.

It is also possible to take a sample of a predetermined amount of fat by melting the fat directly off the carcass or part thereof, thereby avoiding the fat free solids of the lard.

In this embodiment, a sample container may advantageously be used, said sample container comprising a container open at the top and a closing means penetrable by means of an injection needle, characterised in that the open container is divided into an open first chamber and a closed second chamber, the two chambers being separated from each other by means of a partition wall breakable by a slight physical load and that the closing means comprises a third chamber, said chamber having at the top an area penetrable by means of an injection needle and being defined at the bottom by a filter which can be lowered into the container, and that the closing means is provided with a device which breaks the partition wall when applying the closing means.

The boar taint producing indole compounds are advantageously determined by chromatography or fluorometry.

In an embodiment of the invention the contents of the indole compounds in the extract are determined by chromatography, preferably using HPLC (High Performance Liquid Chromatography) with a fluorescence detector or a UV detector.

It is also possible to carry out a direct fluorometric determination on the extract without a chromatographic separation. In this case, the extraction should only be carried out on the fatty phase, i.e. the fat free solids of the lard should be removed prior to the extraction.

Measuring is typically carried out at one or more predetermined emission wavelengths in the range of $340\pm25$ nm and typical excitation wavelengths in the range of $285\pm25$ nm are used. If HPLC with UV detector is used, wavelengths of $225\pm25$ nm or $280\pm25$ nm are used.

In the cases where a chromatographic method is used, the contents of the different indole compounds are determined, whereas by direct fluorometric determination only a total determination of the contents of the indole compounds is obtained. In both cases a precise and reproducible determination of the extent to which the pork will cause an unpleasant smell when prepared later by the consumer is obtained.

The further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention is described in greater details below: with reference to the drawing in which.

DETAILED DESCRIPTION OF THE INVENTION

Figures 1, 2:
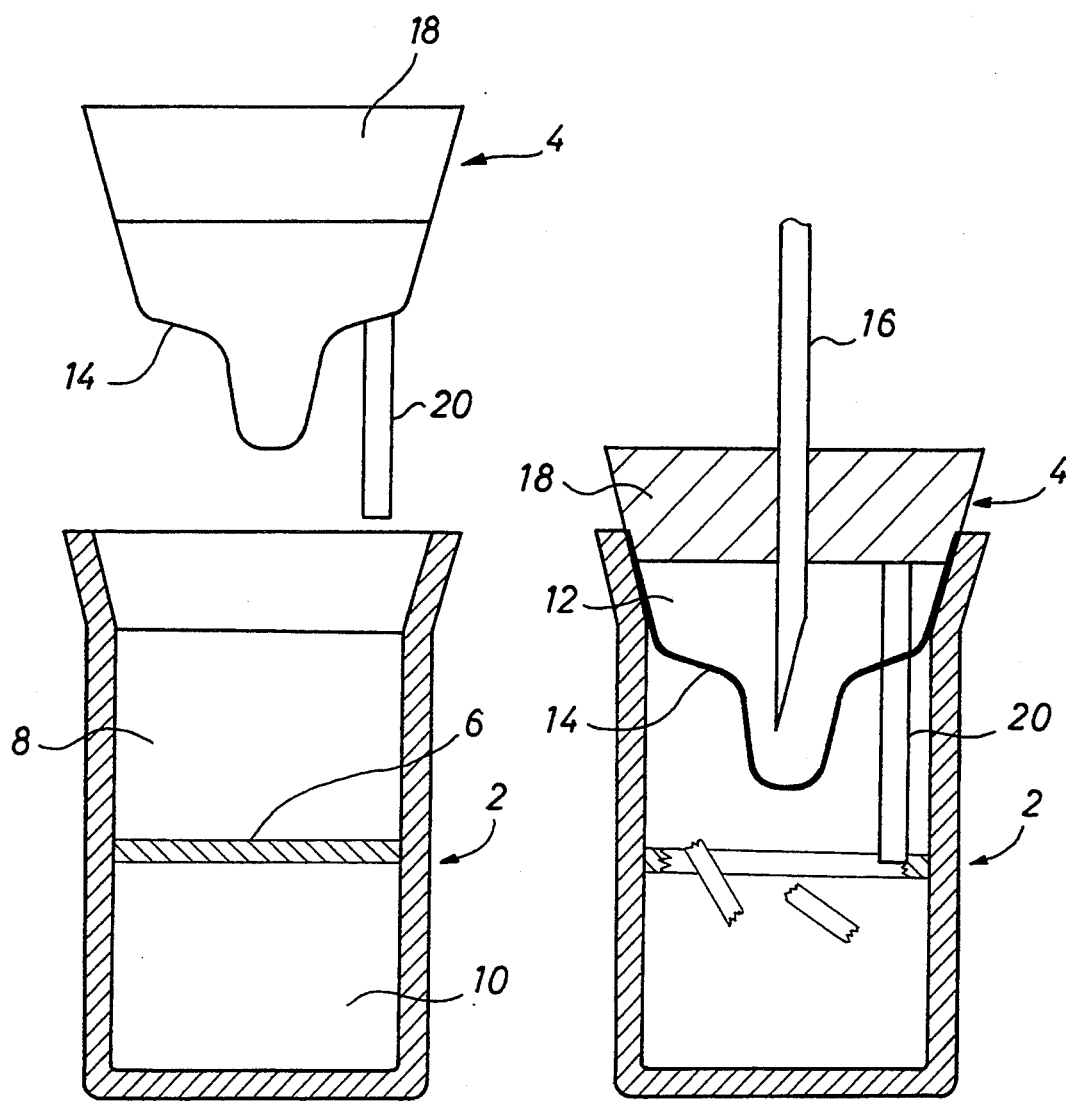
FIG. 1 shows a sample container according to the invention comprising a container and a closing means, partly in sectional view.
FIG. 2 shows the same sample container after the container has been closed by means of the closing means and with an injection needle penetrating the membrane in the closing means.

In one embodiment of the invention a piece of lard is taken from the carcass or part thereof. The lard may advantageously be taken subcutaneously from the occipital region of the animal, where the layer of lard is suitably thick, but in general the contents in the lard of skatole and indole are the same irrespective of from which part of the animal the sample of lard is taken. The measuring results are thus independent of from which part of the carcass the sample has been taken. A defined amount is measured therefrom, either on the basis of volume or weight, the sample being placed in a container. The container with the sample is heated until the fat is melted, for instance in a microwave-oven. The sample now consists of two phases of which one is a liquid fatty phase and the other phase comprises the fat free solids of the lard in the form of a lump of connective tissue, etc.

Subsequently an extractant is added in a predetermined amount relative to the amount of the sample used, for instance in the ratio 1 part by weight of sample to 1 part by volume of extractant (measured in g and ml, respectively). The extractant must be very capable of dissolving the boar taint producing indole compounds, while the fatty phase must be insoluble in the extractant. To ensure a good extraction, the extractant must be able to disperse the fatty phase when simply shaken, while forming an emulsion with a suitable stability. The formation of such an emulsion ensures the contact between the extractant and the fatty phase, which in its turn ensures a reliable extraction of the indole compounds. Any extractant meeting these conditions will be suitable for use by the method according to the invention.

Examples of suitable extractants include polar extractants, such as organic, polar extractants, preferably methanol and ethanol, as well as mixtures thereof with water. Further, the addition of different buffers to adjust the pH value may be advantageous, as well as the addition of other adjuvants, for instance enzymes, according to the extractant chosen.

The sample is extracted for a predetermined minimum period, such as 10 minutes, whereupon the fatty phase and the fat free solids are removed, for instance by filtration, centrifuging or cooling. Subsequently, a chromatographically specific determination of the contents of the sample of the compounds skatole and indole and optionally other boar taint producing indole compounds, for instance by using HPLC with a fluoresence detector or a UV detector, is carried out on the extract.

In an alternative embodiment, a defined amount of liquid fat is decanted and measured into another container immediately after the heating, in which case the previous quantity determination is omitted.

The extraction is then carried out as described for the above embodiment. In addition to a chromatographically specific determination as described above, it is also possible to carry out a total determination of the boar taint producing compounds by means of a direct fluorometric determination on the extract.

In a further embodiment of the invention the fat is melted directly off the carcass by means of a heated object, for instance a soldering iron or a metal tube, in which case a defined amount of fat is melted directly into a container with marked filling height.

The extraction is then carried out as described above and it is also possible in this case to carry out a chromatographic specific determination as well as a total determination of the boar taint producing indole compounds by a direct fluorometric determination.

In connection with the direct melting off of the fat from the carcass, it may be advantageous to use a special sample container as shown in FIGS. 1 and 2. The sample container comprises an open container 2 and a closing means 4 penetrable by an injection needle 16. The open container 2 is divided into two chambers by means of a partition wall 6, an open first chamber 8 and a closed second chamber 10. Each of the chambers 8 and 10 is of a known volume, for instance 2 ml. When using the sample container to carry out the method according to the invention of taking a sample of a predetermined amount of fat by directly melting off the fat from the carcass or part thereof, the melted fat sample is collected in the first chamber 8, the chamber being totally filled whereby after applying the closing means 4, a 2 ml sample has been measured. Prior to the taking of the sample, the second chamber 10 has been filled with the extractant chosen for the analysis, for instance 2 ml of methanol.

The closing means 4, surrounding a third chamber 12, is defined by a tapered filter 14 at the bottom and has been constructed in such a manner at the top that an injection needle may be introduced from the outside and into the third chamber 12. This may for instance be ensured by the chamber 12 at the top being closed by a conventional penetrable membrane 18 of the type used in a conventional capped vial. The closing means 4 is further provided with a breaking means 20 to break the partition wall 6 when applying the closing means to the open container 2.

The sample container is used in the following manner: The closing means is applied to the container after the first chamber 8 has been filled with the fat sample, whereby the exact volume of the fat sample is limited and the partion wall 6 is broken. The fat sample and the extractant are then mixed by shaking the sample container. The extractant with dissolved components is filtered through the filter 14 and can subsequently be taken up by means of an injection needle 16 which is introduced directly into the analytical apparatus used.

The sample container may also be constructed in such a manner that when the closing means is applied, an overpressure sufficient to break the partition wall is generated. In addition to the extractant, a volume of compressible gas, for instance air, may also be present in the second chamber, whereby following the breakage of the partition wall there will be a certain overpressure in the container. Such overpressure may support the transfer of filtrate through the filter into the third chamber.

The method according to the invention is conventionally carried out by heating the sample until the fat is liquid before carrying out the extraction. However, it is also possible to add the required amount of extractant prior to the heating, whereby the method is carried out by heating a mixture of the sample and the extractant.

The following Examples further illustrate the invention.

EXAMPLE 1

The present Example illustrates the extraction on the entire sample of lard and the determination of indole and skatole by HPLC.

A sample of lard of 5 g is taken subcutaneously from the occipital region of a carcass. The sample is placed in a container and heated at 80° C. for 10 minutes in microwave oven in order to melt the fat. An amount of 5 ml of methanol is then added to the sample which is shaken, whereupon the sample is extracted for 10 minutes. Subsequently, the sample is filtered to remove the fat and connective tissue and analyzed by HPLC under the following conditions:

HPLC-apparatus: Merck HPLC with fluorescence detector and autosampler,
Eluant: water:methanol (20:80) (volume:volume)
Flow: 1 ml/minute
Fluorescence detector: excitation wavelength=285 nm, emission wavelength=340 nm
Column: Lichrocart 250-4, Lichrospher 100 RP18, 5 micron, reverse phase
Injection volume: 20 microliter,
Retention time: skatole 4 minutes, indole 3.5 minutes
Detection limit: 5 ppb (0,005 ppm) in solution
Measuring uncertainty less than 5% at concentrations larger than 48 ppb of the extract.

A total of 5 tests were carried out to determine the concentration of skatole and indole (measured in ppb) of the extract from lard and the results thereof are stated in Table 1 below.

EXAMPLE 2

The present Example illustrates the extraction on a sample of lard, from which the fat free solids (connective tissue, etc.) of the lard have been removed, and subsequent HPLC analysis to determine skatole and indole.

A piece of lard is taken subcutaneously from the occipital region of a carcass. The lard is placed in a container and heated at 80° C. for 10 minutes in a microwave-oven until the fat has melted. 5 ml of liquid fat are subsequently decanted and measured into another container, to which 5 ml of methanol are added. Following the shaking, extraction is carried out of 10 minutes and the sample is filtered to remove fat particles, whereupon the extract is analyzed by HPLC under the same conditions as described in Example 1.

A total of 5 determinations were carried out and the results thereof are stated in Table 1 below.

EXAMPLE 3

The present Example illustrates the direct melting off of fat from a carcass and subsequent determination of skatole and indole by HPLC.

A hot object in the form of a metal tube having a temperature of about 150° C. is placed on the occipital region of a carcass, whereby the fat is melted directly from the carcass and runs through the metal tube into a measuring container, until 5 ml have been measured. 5 ml of methanol are added to said melted fat sample, followed by shaking. After extracting for 10 minutes, the sample is filtered and the extract is analyzed by HPLC under the same conditions as described in Example 1.

EXAMPLE 4

The present Example is carried out as described for Example 2, except that instead of a HPLC analysis, a direct fluorometric determination on the filtrate is carried out using a fluorometer (SHIMADZU MODEL RF-5000, Shimadzu, Kyoto, Japan) at the same excitation wavelength and emission wavelength as for HPLC.

EXAMPLE 5

The present Example illustrates the direct melting off of fat and subsequent determination of skatole and indole by HPLC, where the sample container shown in FIGS. 1 and 2 is used.

The sample container used comprises a container and a closing means as shown in FIG. 1. The container is a glass container with a total volume of 4 ml. The container is filled with 2 ml methanol as extractant. Above the methanol a partition wall of glass is arranged.

The sampling is carried out by introducing an electricly heated metal tube having a temperature of 150° C. into the carcass as described in Example 3. From the metal tube the sample of melted fat is passed directly into the first chamber of the container, i.e. the chamber above the partition wall. Alternatively, the taking of the sample and the melting of the fat are carried out as described in Example 2, the first chamber of the container being filled with the decanted, melted sample of fat.

Subsequently a stopper is applied, said stopper conventionally being constructed in such a manner that an injection needle may be introduced through an area of the stopper in order to collect an analytical sample for HPLC. The stopper is further provided with a tapered filter, defining a third chamber. Furthermore, the stopper is provided with a rod extending downwards.

When applying the stopper, a defined amount of the sample of fat of 2 ml is enclosed and the downwards extending rod is pressed into the glass partition wall, which is thereby broken. The sample of fat and the methanol may subsequently be mixed by shaking the closed container. Before the sample container reaches the final HPLC analysis, the amount of the sample required for the analysis has filtered into the third chamber. A sample for HPLC analysis may thereby be taken by means of an injection needle in a conventional manner. In practice, the sample container may be placed directly in the auto sampler of the HPLC analytical apparatus.

When taking the sample of fat, the sample container may advantageously be provided with a number in the form of a bar code. Immediately prior to injecting the sample to be analyzed into the HPLC apparatus, the bar code is read automatically. This makes possible electronic coordination of the number of the carcass and the analytical result to be used when physically sorting out the carcasses. In this manner the analytical result may be coordinated with the other slaughtering data and used for the necessary sorting and when settling the account with the breeder.

Comparison Tests

To show the favourable results obtained when melting the fat before carrying out the extraction, a comparison test has been carried out as described below:

5 determinations were carried out using the methods according to the invention as described in Examples 1 and 2, using the method described in Example 1 except that the sample of lard was not heated to melt the fat prior to the extraction, and using the spectrophotometric method for the detection of skatole equivalents described in Danish patent No. 154,667, respectively. In the above four methods, the samples were taken from the same animal. The results appear from Table 1.

TABLE 1

| | Concentrations of skatole and indole in extract from lard | | | | | | |
|---|---|---|---|---|---|---|---|
| | Comparison test HPLC-analysis Extracted lard without heating | | Embodiment acc. to Ex. 1 HPLC-analysis Extracted lard with heating | | Embodiment acc. to Ex. 2 HPLC-analysis Extracted fat with heating | | Comparison test Spectrophotometry Extracted lard (cf. DK 154.667) |
| Sample No. | Skatole (ppb) | Indole (ppb) | Skatole (ppb) | Indole (ppb) | Skatole (ppb) | Indole (ppb) | Skatole equiv. (ppm) |
| 1 | 0 | 0 | 17 | 9 | 23 | 8 | 0.10 |
| 2 | 0 | 0 | 47 | 14 | 57 | 18 | 0.23 |
| 3 | 0 | 0 | 81 | 16 | 116 | 19 | 0.30 |
| 4 | 0 | 0 | 136 | 82 | 192 | 108 | 0.44 |
| 5 | 0 | 0 | 232 | 133 | 265 | 145 | 0.66 |

The reason for the different measuring values for the embodiment according to Example 1, the embodiment according to Example 2 and the comparison test according to DK patent No. 154.667, respectively, is that different test parameters have been used. The good correspondence between these analytical methods may be seen from the good linear correlation between the measuring results for the three methods.

As appears from the comparison test in the Table, it was not possible to detect either skatole or indole when the extraction was carried out without prior heating. If the sample of lard was heated to melt the fat before the extraction, it proved possible to detect both skatole and indole.

Surprisingly, it is only possible to extract skatole and indole from lard if a preceding heating of the lard (melting of the fat) is carried out.

The results otherwise obtained correspond very well with the results obtained by the spectrophotometric method for the determination of skatole equivalents disclosed in DK patent No. 154,667. It should be understood that the measuring results obtained by the method according to the invention do not express 100% real values, but that the values may be related to the degree of boar taint, whereby at fixed test conditions a value may be established as a limit for rejecting the pork. The values may further be correlated to other measuring results known to be associated to the degree of boar taint. If, in this manner, the skatole concentrations obtained by the embodiment according to Example 1 and the embodiment according to Example 2 are compared to the spectrophotometric measuring results obtained by the method disclosed in DK patent No. 154.667, correlation factors of almost 1.000, that is 0.995 and 0.988, 5respectively, are obtained.

Therefore, to a high degree the measuring results depend on the test parameters used, such as the choice of extractant, and as is seen from the Table, the embodiment according to Example 2 yields higher values, as the analysis is only carried out on fat not containing fat free solids in the form of connective tissue etc., which does not contribute to the content of skatole and indole.

To show the reproducibility of the method, 4 samples of lard of 5 g each and 3 samples of lard of 5 g each were taken from 2 samples of lard each in the manner described in Example 1. The samples were such analyzed 10 times.

The results appear in Tables 2 and 3 below.

TABLE 2

| | ppb skatole at HPCL-analysis | | | | | | |
|---|---|---|---|---|---|---|---|
| | Sample | | | | | | |
| Analysis | 1 | 2 | 3 | 4 | Average | Std. | Std. % |
| 1 | 44.80 | 48.27 | 51.47 | 51.87 | | | |
| 2 | 46.27 | 48.93 | 51.87 | 45.87 | | | |
| 3 | 48.93 | 47.60 | 52.80 | 46.67 | | | |
| 4 | 50.00 | 49.07 | 49.73 | 50.40 | | | |
| 5 | 48.40 | 50.93 | 49.07 | 43.87 | | | |
| 6 | 47.47 | 46.40 | 49.20 | 50.27 | | | |
| 7 | 44.13 | 50.40 | 50.93 | 49.07 | | | |
| 8 | 47.73 | 45.60 | 49.73 | 49.33 | | | |
| 9 | 49.07 | 43.87 | 49.33 | 47.60 | | | |
| 10 | 49.33 | 45.20 | 52.53 | 44.67 | | | |
| Average | 47.61 | 47.63 | 50.67 | 47.96 | 48.47 | 1.28 | 2.64 |
| Std. | 1.87 | 2.20 | 1.36 | 2.52 | | | |
| Std. % | 3.93 | 4.62 | 2.68 | 5.25 | 4.12 | | |
| Lowest | 44.13 | 43.87 | 49.07 | 43.87 | | | |
| Highest | 50.00 | 50.93 | 52.80 | 51.87 | | | |
| All: n = 40 | | | | | | | |
| Average | 48.47 | | | | | | |
| Std. | 2.40 | | | | | | |
| Dev. in % | 4.95 | | | | | | |

4 samples of lard from the same pig each analyzed 10 times.

TABLE 3

| | ppb skatole at HPLC-analysis | | | | | |
|---|---|---|---|---|---|---|
| | Sample | | | | | |
| Analysis | 1 | 2 | 3 | Average | Std. | Std. % |
| 1 | 72.00 | 74.67 | 72.00 | | | |
| 2 | 69.33 | 74.67 | 69.33 | | | |
| 3 | 72.00 | 69.33 | 72.00 | | | |
| 4 | 74.67 | 66.67 | 69.33 | | | |
| 5 | 69.33 | 72.00 | 72.00 | | | |
| 6 | 74.67 | 66.67 | 66.67 | | | |
| 7 | 77.33 | 66.67 | 69.33 | | | |
| 8 | 74.67 | 69.33 | 72.00 | | | |
| 9 | 77.33 | 69.33 | 69.33 | | | |
| 10 | 74.67 | 72.00 | 72.00 | | | |
| Average | 73.60 | 70.13 | 70.40 | 71.38 | 1.58 | 2.21 |
| Std. | 2.72 | 2.93 | 1.77 | | | |
| Std. % | 3.69 | 4.18 | 2.51 | 3.46 | | |
| Lowest | 69.33 | 66.67 | 66.67 | | | |
| Highest | 77.33 | 74.67 | 72.00 | | | |
| All: n = 30 | | | | | | |
| Average | 71.38 | | | | | |
| Std. | 2.98 | | | | | |
| Dev. in % | 4.17 | | | | | |

3 samples of lard from the same pig each analyzed 10 times

As appears from the Tables, the method is very accurate and a standard deviation of 4.95% is obtained at a measuring value of about 50 ppb, cf. Table 2, and a standard deviation of 4.17% at a measuring value of about 70 ppb, cf. Table 3.

The present method is specific, accurate and reproducible. By the method it is thus possible with a high certainty to identify the pigs which, when subsequently prepared by the consumer, will display an unpleasant boar taint. The method is highly usable for small slaughterhouses where, for instance, up to about 500 analyses are to be made per day, as the method is relatively inexpensive and does not require investments in expensive analytical equipment. As mentioned above, the method is very accurate as it may be carried out with a measuring uncertainty of less than 5% in the relevant range of measurement. As mentioned previously, the limit for rejecting pigs in Danish slaughterhouses has been set at 0.25 ppm skatole equivalents determined by the method dealt with in DK patent No. 154,667, which by the method described in Example 1 would correspond to a measuring value of about 65 ppb skatole. The rejection limit chosen in practice may easily be determined by the person skilled in the art on the basis of routine experiments.

By heating to melt the fat prior to the extraction, it has surprisingly proved possible to detect both skatole, indole and other potentially boar taint producing indole compounds. Of other potentially boar taint producing indole compounds, indole acetic acid (IAA) and tryptophan may possibly play a role, as both compounds may be broken down to skatole. The reason why the heating has proved so efficient is thought to be that the relevant compounds are traditionally found in the lard in conjugated form, possibly bound to the fatty acids, and that when heated they are released therefrom.

BEST MODE FOR CARRYING OUT THE INVENTION

The presently best embodiment of the invention is the method described in Example 3 using a sample container as described in Example 5.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:
1. A method for determining indole compounds associated with boar taint in pork wherein the method comprises the steps of:
   a) obtaining a sample of a predetermined amount of lard or fat from a carcass of a pig or part thereof,
   b) heating the sample to melt fat in the sample,
   c) extracting at least a portion of the sample with a polar solvent and
   d) determining the contents of one or more indole compounds in the extract in that

2. A method as claimed in claim 1, wherein the entire sample of lard or fat is extracted.

3. A method as claimed in claim 1, wherein prior to the extraction the sample is separated into a fat free solids fraction and a liquid fatty phase fraction and wherein the extraction is only carried out on the liquid fatty phase fraction.

4. A method as claimed in claim 1, wherein a sample of a predetermined amount of fat is taken by directly melting off the fat from the carcass or part thereof.

5. A method as claimed in claim 3 or 4, wherein following the extraction the contents of the indole compounds in the extract are determined by direct fluorometric determination.

6. A method as claimed in claim wherein the fluorometric determination is made using one or more predetermined emission wavelengths of between 315 and 365 nm, and using one or more predetermined excitation wavelengths of between 260 and 310 nm.

7. A method as claimed in claim 1, wherein following the extraction, the contents of the indole compounds in the extract are determined by chromatography or fluorometry.

8. A method as claimed in claim 7, wherein following the extraction the contents of the indole compounds in the extract are determined by chromatography using HPLC with a fluorescence detector or UV detector.

9. A method as claimed in claim 8, wherein HPLC with a UV detector is employed at a wavelength of between either 200 and 250 nm or 255 and 305 nm.

10. A method as claimed in claim 1, wherein the heating and extraction steps are performed simultaneously.

11. A method as claimed in claim 1, wherein the extraction step follows the step of heating the sample until the lard or fat is liquid.

12. A method as claimed in claim 1, wherein the indole compounds comprise skatole and indole.

13. A method for determining indole compounds associated with boar taint in pork comprising the steps of:
   a) providing melted fat from the pork in a open first chamber of a container having said first chamber and a second chamber containing a polar solvent, the two chambers initially being separated from each other by means of a partition wall,
   b) closing the first chamber by the use of a closing means comprising a third chamber, the third chamber then being separated from the first chamber by a filter,
   c) breaking the partition wall and mixing the polar solvent with the fat to extract the indole compounds,
   d) introducing the extract into said third chamber through said filter,
   e) penetrating the third chamber by using an injection needle and
   f) withdrawing a sample therefrom and determining the contents of the one or more indole compounds in the sample.

* * * * *